US012558538B2

(12) United States Patent
Ben-Tov Kuperberg et al.

(10) Patent No.: US 12,558,538 B2
(45) Date of Patent: Feb. 24, 2026

(54) USING STAGGERED CHANGES IN AMPLITUDE AND FREQUENCY TO AMELIORATE ELECTROSENSATION DURING TREATMENT WITH ALTERNATING ELECTRIC FIELDS

(71) Applicant: Novocure GmbH, Root (CH)

(72) Inventors: Mor Ben-Tov Kuperberg, Haifa (IL);
Yoram Wasserman, Haifa (IL);
Michael Shtotland, Haifa (IL)

(73) Assignee: Novocure GmbH, Baar (CH)

( * ) Notice: Subject to any disclaimer, the term of this patent is extended or adjusted under 35 U.S.C. 154(b) by 0 days.

(21) Appl. No.: 18/897,207

(22) Filed: Sep. 26, 2024

(65) Prior Publication Data

US 2025/0108212 A1 Apr. 3, 2025

Related U.S. Application Data

(60) Provisional application No. 63/541,347, filed on Sep. 29, 2023.

(51) Int. Cl.
*A61N 1/36* (2006.01)
*A61N 1/02* (2006.01)
*A61N 1/04* (2006.01)
(52) U.S. Cl.
CPC ......... *A61N 1/36002* (2017.08); *A61N 1/025* (2013.01); *A61N 1/0408* (2013.01)
(58) Field of Classification Search
None
See application file for complete search history.

(56) References Cited

U.S. PATENT DOCUMENTS

| | | | |
|---|---|---|---|
| 6,868,289 B2 | 3/2005 | Palti | |
| 7,016,725 B2 | 3/2006 | Palti | |
| 7,089,054 B2 | 8/2006 | Palti | |

(Continued)

FOREIGN PATENT DOCUMENTS

DE 10100385 A1 * 7/2002 ............. A61N 1/326

OTHER PUBLICATIONS

DE10100385A-translation (Year: 2002).*
International Search Report and Written Opinion issued in application No. PCT/IB2024/059373 dated Dec. 17, 2024.

*Primary Examiner* — Manuel A Mendez
(74) *Attorney, Agent, or Firm* — Potomac Law Group, PLLC

(57) ABSTRACT

When transducer arrays (i.e., arrays of electrode elements) are used to apply alternating electric fields (e.g., TTFields) to a subject's body, the subject may experience electrosensation. This electrosensation can be ameliorated by (a) increasing the amplitude of the field in a series of steps, and allowing some time to pass for the subject to acclimate to each step before the amplitude is increased to the next-higher value, (b) starting out at a frequency that is higher than the recommended frequency for each indication (e.g., higher than 200 kHz for treating glioblastoma), subsequently decreasing the frequency to the recommended frequency in a series of steps, and allowing some time to pass for the subject to acclimate to each step before the frequency is decreased to the next-lower value, and (c) avoiding (or at least minimizing) situations in which an increase in amplitude and a decrease in frequency occur simultaneously.

10 Claims, 4 Drawing Sheets

(56) References Cited

U.S. PATENT DOCUMENTS

| | | | |
|---|---|---|---|
| 7,136,699 B2 | 11/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 * | 2/2011 | Palti | A61N 1/40 |
| | | | 607/76 |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 8,948,875 B2 * | 2/2015 | Paulus | A61N 1/36025 |
| | | | 607/45 |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 10,967,167 B2 | 4/2021 | Hagemann et al. | |
| 11,103,698 B2 | 8/2021 | Chang et al. | |
| 11,191,956 B2 | 12/2021 | Giladi et al. | |
| 11,395,916 B2 | 7/2022 | Wasserman et al. | |
| 11,654,279 B2 | 5/2023 | Wasserman et al. | |
| 2004/0176804 A1 | 9/2004 | Palti | |
| 2005/0004628 A1 * | 1/2005 | Goetz | A61N 1/37252 |
| | | | 607/60 |
| 2005/0209642 A1 | 9/2005 | Palti | |
| 2006/0167499 A1 | 7/2006 | Palti | |
| 2006/0276858 A1 | 12/2006 | Palti | |
| 2007/0225766 A1 | 9/2007 | Palti | |
| 2007/0239213 A1 | 10/2007 | Palti | |
| 2009/0076366 A1 | 3/2009 | Palti | |
| 2010/0324547 A1 | 12/2010 | Palti | |
| 2011/0137229 A1 | 6/2011 | Palti et al. | |
| 2012/0029419 A1 | 2/2012 | Palti | |
| 2012/0283726 A1 | 11/2012 | Palti | |
| 2012/0290048 A1 * | 11/2012 | Marc | A61N 1/403 |
| | | | 607/98 |
| 2014/0330268 A1 | 11/2014 | Palti et al. | |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0280687 A1 | 10/2018 | Carter et al. | |
| 2019/0117956 A1 | 4/2019 | Wenger et al. | |
| 2019/0117963 A1 | 4/2019 | Travers et al. | |
| 2019/0117970 A1 | 4/2019 | Schmidt et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0114141 A1 | 4/2020 | Bomzon et al. | |
| 2020/0114142 A1 | 4/2020 | Bomzon et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0269037 A1 | 8/2020 | Hagemann et al. | |
| 2020/0269041 A1 | 8/2020 | Zeevi et al. | |
| 2020/0269042 A1 | 8/2020 | Giladi et al. | |
| 2020/0368525 A1 | 11/2020 | Maag et al. | |
| 2021/0031031 A1 | 2/2021 | Wasserman et al. | |
| 2021/0038584 A1 | 2/2021 | Voloshin-Sela | |
| 2021/0060334 A1 | 3/2021 | Avraham et al. | |
| 2021/0069503 A1 | 3/2021 | Tran et al. | |
| 2021/0138233 A1 | 5/2021 | Deslauriers | |
| 2021/0162228 A1 | 6/2021 | Urman et al. | |
| 2021/0177492 A1 | 6/2021 | Travers et al. | |
| 2021/0187277 A1 | 6/2021 | Wasserman et al. | |
| 2021/0196348 A1 | 7/2021 | Wasserman | |
| 2021/0196967 A1 | 7/2021 | Carlson et al. | |
| 2021/0199640 A1 | 7/2021 | Patel et al. | |
| 2021/0202179 A1 | 7/2021 | Saito et al. | |
| 2021/0203250 A1 | 7/2021 | Wasserman et al. | |
| 2021/0268247 A1 | 9/2021 | Story et al. | |
| 2021/0299439 A1 | 9/2021 | Shamir et al. | |
| 2021/0299440 A1 | 9/2021 | Deslauriers et al. | |
| 2021/0308446 A1 | 10/2021 | Alon et al. | |
| 2021/0330950 A1 | 10/2021 | Hagemann et al. | |
| 2021/0346694 A1 | 11/2021 | Wasserman et al. | |
| 2021/0379362 A1 | 12/2021 | Smith et al. | |
| 2021/0408383 A1 | 12/2021 | Kalra et al. | |
| 2022/0088403 A1 | 3/2022 | Voloshin-Sela et al. | |
| 2022/0095997 A1 | 3/2022 | Wasserman | |
| 2022/0096821 A1 | 3/2022 | Kirson et al. | |
| 2022/0096829 A1 | 3/2022 | Farber et al. | |
| 2022/0118249 A1 | 4/2022 | Bomzon et al. | |
| 2022/0161028 A1 | 5/2022 | Giladi et al. | |
| 2022/0193435 A1 | 6/2022 | Wasserman et al. | |
| 2022/0203111 A1 | 6/2022 | Carlson et al. | |
| 2022/0267445 A1 | 8/2022 | Tran et al. | |
| 2022/0280787 A1 | 9/2022 | Bomzon et al. | |
| 2022/0288395 A1 | 9/2022 | Voloshin-Sela et al. | |
| 2022/0313992 A1 | 10/2022 | Wasserman | |
| 2022/0323753 A1 | 10/2022 | Voloshin-Sela et al. | |
| 2022/0387784 A1 | 12/2022 | Kirson et al. | |
| 2022/0409893 A1 | 12/2022 | Wasserman et al. | |
| 2023/0098801 A1 | 3/2023 | Carlson | |
| 2023/0201616 A1 | 6/2023 | Carlson | |
| 2024/0139505 A1 | 5/2024 | Wasserman | |
| 2024/0149053 A1 | 5/2024 | Kirson et al. | |
| 2024/0169536 A1 | 5/2024 | Shamir et al. | |
| 2024/0207604 A1 | 6/2024 | Deslauriers | |
| 2024/0216679 A1 | 7/2024 | Wasserman et al. | |
| 2024/0216684 A1 | 7/2024 | Wasserman et al. | |
| 2024/0216685 A1 | 7/2024 | Wasserman et al. | |
| 2024/0219367 A1 | 7/2024 | Wasserman et al. | |
| 2024/0238588 A1 | 7/2024 | Bomzon et al. | |
| 2024/0325739 A1 | 10/2024 | Wasserman et al. | |
| 2024/0325753 A1 | 10/2024 | Levi | |
| 2024/0325768 A1 | 10/2024 | Ben-Tov Kuperberg et al. | |

(56)        References Cited

U.S. PATENT DOCUMENTS

| 2024/0350799 | A1 | 10/2024 | Tran et al. |
| 2025/0001194 | A1 | 1/2025 | Carlson |

* cited by examiner

USING STAGGERED CHANGES IN AMPLITUDE AND FREQUENCY TO AMELIORATE ELECTROSENSATION DURING TREATMENT WITH ALTERNATING ELECTRIC FIELDS

CROSS REFERENCE TO RELATED APPLICATIONS

This Application claims the benefit of U.S. Provisional Application 63/541,347, filed Sep. 29, 2023, which is incorporated herein by reference in its entirety.

BACKGROUND

Tumor Treating Fields (TTFields) therapy is a proven approach for treating tumors using alternating electric fields at frequencies between 50 kHz and 5 MHz (e.g., 150-200 kHz). In the prior art Optune® system, TTFields are delivered to patients via four transducer arrays that are placed on the patient's skin near the tumor. The transducer arrays are arranged in two pairs, with one pair of transducer arrays positioned to the left and right of the tumor, and the other pair of transducer arrays positioned anterior and posterior to the tumor. Each transducer array is connected via a multi-wire cable to an AC signal generator. The AC signal generator (a) sends an AC current through the anterior/posterior (A/P) pair of transducer arrays for 1 second, which induces an electric field with a first direction through the tumor; then (b) sends an AC current through the left/right (L/R) pair of arrays for 1 second, which induces an electric field with a second direction through the tumor; then repeats steps (a) and (b) for the duration of the treatment. Each transducer array includes a plurality (e.g., between 9 and 30) of electrode elements.

Alternating electric fields can also be used to treat medical conditions other than tumors. For example, as described in U.S. Pat. No. 10,967,167 (which is incorporated herein by reference in its entirety), alternating electric fields can be used to increase the permeability of the blood brain barrier (BBB) so that, e.g., chemotherapy drugs can reach the brain.

When treating a subject using alternating electric fields, a specific frequency is typically recommended for each indication (e.g., 200 kHz for treating glioblastoma, 150 kHz for treating mesothelioma, 75 kHz-100 kHz for increasing the permeability of the BBB, etc.). In addition, higher amplitudes are strongly associated with higher efficacy of treatment. However, as the amplitude of the alternating electric field increases, and/or as the frequency of the alternating electric field decreases, some subjects experience an electrosensation effect. This electrosensation could be, for example, a vibratory sensation, paresthesia, and/or a twitching or contraction sensation of muscle fibers, or a flicker of light in the eyes (phosphene). Electrosensation may discourage some subjects from continuing their treatment using alternating electric fields. Furthermore, electrosensation can limit the amplitude of the alternating electric fields that can comfortably be applied to the given subject at any given frequency, which in turn can limit the efficacy of the treatment.

SUMMARY OF THE INVENTION

One aspect of the invention is directed to a first apparatus for applying electrical signals to first, second, third and fourth sets of at least one electrode element. The first apparatus comprises an AC signal generator and a controller.

The AC signal generator has a first output, a second output, and at least one control input. And the AC signal generator is configured so that the at least one control input controls an amplitude of the first output, a frequency of the first output, an amplitude of the second output, and a frequency of the second output. The controller is configured to apply a sequence of control signals to the at least one control input of the AC signal generator, wherein the sequence of control signals controls the AC signal generator so that (a) when the first output is activated at a given time, the first output has an initial amplitude and an initial frequency, (b) at a first set of times that follow the given time while the first output remains active, the amplitude of the first output increases while the frequency of the first output remains constant, and (c) at a second set of times that follow the given time while the first output remains active, the frequency of the first output decreases while the amplitude of the first output remains constant, wherein the first set of times and the second set of times are mutually exclusive. The sequence of control signals further controls the AC signal generator so that (a) when the second output is activated at a certain time, the second output has an initial amplitude and an initial frequency, (b) at a third set of times that follow the certain time while the second output remains active, the amplitude of the second output increases while the frequency of the second output remains constant, and (c) at a fourth set of times that follow the certain time while the second output remains active, the frequency of the second output decreases while the amplitude of the second output remains constant, wherein the third set of times and the fourth set of times are mutually exclusive. The sequence of control signals causes the AC signal generator to (i) activate the first output for an interval of time, (ii) subsequently activate the second output for an interval of time, and (iii) subsequently repeat (i) and (ii) at least 10 times in an alternating sequence.

In some embodiments of the first apparatus, each first set of times includes at least 10 times, each second set of times includes at least 3 times, each third set of times includes at least 10 times, and each fourth set of times includes at least 3 times. In some embodiments of the first apparatus, each first set of times includes at least 50 times, each second set of times includes at least 3 times, each third set of times includes at least 50 times, and each fourth set of times includes at least 3 times. In some embodiments of the first apparatus, each interval of time when the first output is activated has a duration of at least 800 ms, and each interval of time when the second output is activated has a duration of at least 800 ms. In some embodiments of the first apparatus, each first set of times and a respective second set of times are interspersed with each other, and each third set of times and a respective fourth set of times are interspersed with each other.

In some embodiments of the first apparatus, the initial frequency of the first output is at least 50% higher than a final frequency of the first output, and the initial frequency of the second output is at least 50% higher than a final frequency of the second output. Optionally, in these embodiments, the final frequency of both the first and second outputs is between 75 kHz and 300 kHz.

In some embodiments of the first apparatus, each first set of times includes at least 50 times, each second set of times includes at least 3 times, each third set of times includes at least 50 times, and each fourth set of times includes at least 3 times; each interval of time when the first output is activated has a duration of at least 2 seconds; each interval of time when the second output is activated has a duration of at least 2 seconds; each first set of times and a respective second set of times are interspersed with each other; each third set of times and a respective fourth set of times are interspersed with each other; the initial frequency of the first output is at least 50% higher than a final frequency of the first output; and the initial frequency of the second output is at least 50% higher than a final frequency of the second output. Optionally, in these embodiments, the final frequency of both the first and second outputs is between 75 kHz and 300 kHz.

Another aspect of the invention is directed to a second apparatus for applying electrical signals to first and second sets of at least one electrode element. The second apparatus comprises an AC signal generator and a controller. The AC signal generator has an output and at least one control input, and the AC signal generator is configured so that the at least one control input controls an amplitude of the output and a frequency of the output. The controller is configured to apply a sequence of control signals to the at least one control input of the AC signal generator, wherein the sequence of control signals controls the AC signal generator so that (a) when the output is activated at a given time, the output has an initial amplitude and an initial frequency, (b) at a first set of times that follow the given time while the output remains active, the amplitude of the output increases while the frequency of the output remains constant, and (c) at a second set of times that follow the given time while the output remains active, the frequency of the output decreases while the amplitude of the output remains constant. The first set of times and the second set of times are mutually exclusive.

In some embodiments of the second apparatus, the first set of times includes at least 10 times; the second set of times includes at least 3 times; the first set of times and the second set of times are interspersed with each other; the initial frequency of the output is at least 50% higher than a final frequency of the output; and the final frequency of the output is between 75 kHz and 300 kHz.

Another aspect of the invention is directed to a first method for applying alternating electric fields to a target region of a subject's body. The first method comprises (i) imposing a first alternating electric field with a first orientation in the target region for an interval of time, wherein the first alternating electric field has a frequency and an average amplitude that vary over time such that (a) when the first alternating electric field is activated at a given time, the first alternating electric field has an initial average amplitude and an initial frequency, (b) at a first set of times that follow the given time while the first alternating electric field remains active, the average amplitude of the first alternating electric field increases while the frequency of the first alternating electric field remains constant, and (c) at a second set of times that follow the given time while the first alternating electric field remains active, the frequency of the first alternating electric field decreases while the average amplitude of the first alternating electric field remains constant, wherein the first set of times and the second set of times are mutually exclusive; (ii) subsequently imposing a second alternating electric field with a second orientation in the target region for an interval of time, wherein the second alternating electric field has a frequency and an average amplitude that vary over time such that (a) when the second alternating electric field is activated at a certain time, the second alternating electric field has an initial average amplitude and an initial frequency, (b) at a third set of times that follow the certain time while the second alternating electric field remains active, the average amplitude of the second alternating electric field increases while the frequency of the second alternating electric field remains constant, and (c) at a fourth set of times that follow the certain time while the second alternating electric field remains active, the frequency of the second alternating electric field decreases while the average amplitude of the second alternating electric field remains constant, wherein the third set of times and the fourth set of times are mutually exclusive; and (iii) subsequently repeating steps (i) and (ii) at least 10 times in an alternating sequence.

In some instances of the first method, each first set of times includes at least 10 times, each second set of times includes at least 3 times, each third set of times includes at least 10 times, and each fourth set of times includes at least 3 times. In some instances of the first method, each first set of times includes at least 50 times, each second set of times includes at least 3 times, each third set of times includes at least 50 times, and each fourth set of times includes at least 3 times.

In some instances of the first method, each interval of time when the first alternating electric field is imposed has a duration of at least 800 ms, and each interval of time when the second alternating field is imposed has a duration of at least 800 ms. In some instances of the first method, each first set of times and a respective second set of times are interspersed with each other, and each third set of times and a respective fourth set of times are interspersed with each other.

In some instances of the first method, the initial frequency of the first alternating field is at least 50% higher than a final frequency of the first alternating field, and the initial frequency of the second alternating field is at least 50% higher than a final frequency of the second alternating field. Optionally, in these instances, the final frequency of both the first and second alternating electric fields is between 75 kHz and 300 kHz.

In some instances of the first method, each first set of times includes at least 50 times, each second set of times includes at least 3 times, each third set of times includes at least 50 times, and each fourth set of times includes at least 3 times; each interval of time when the first alternating electric field is imposed has a duration of at least 2 seconds; each interval of time when the second alternating electric field is imposed has a duration of at least 2 seconds; each first set of times and a respective second set of times are interspersed with each other; each third set of times and a respective fourth set of times are interspersed with each other; the initial frequency of the first alternating electric field is at least 50% higher than a final frequency of the first alternating electric field; and the initial frequency of the second alternating electric field is at least 50% higher than a final frequency of the second alternating electric field. Optionally, in these instances, the final frequency of both the first and second alternating electric fields is between 75 kHz and 300 kHz.

Another aspect of the invention is directed to a second method for applying alternating electric fields to a target region of a subject's body. The second method comprises imposing an alternating electric field in the target region for an interval of time, wherein the alternating electric field has a frequency and an average amplitude that vary over time such that (a) when the alternating electric field is activated at a given time, the alternating electric field has an initial average amplitude and an initial frequency, (b) at a first set of times that follow the given time while the alternating electric field remains active, the average amplitude of the alternating electric field increases while the frequency of the alternating electric field remains constant, and (c) at a second set of times that follow the given time while the alternating electric field remains active, the frequency of the alternating electric field decreases while the average amplitude of the alternating electric field remains constant. The first set of times and the second set of times are mutually exclusive.

In some instances of the second method, one or more of the following are present: the first set of times includes at least 10 times; the second set of times includes at least 3 times; the first set of times and the second set of times are interspersed with each other; the initial frequency of the alternating field is at least 50% higher than a final frequency of the alternating field; and the final frequency of the alternating field is between 75 kHz and 300 kHz.

Another aspect of the invention is directed to a third method for applying alternating electric fields to a target region of a subject's body. The third method comprises imposing a first alternating electric field with a first orientation in the target region for an interval of time, wherein the first alternating electric field has a frequency and an average amplitude that vary over time such that (a) when the first alternating electric field is activated at a given time, the first alternating electric field has an initial average amplitude and an initial frequency, (b) at a first set of times that follow the given time while the first alternating electric field remains active, the average amplitude of the first alternating electric field increases while the frequency of the first alternating electric field remains constant, and (c) at a second set of times that follow the given time while the first alternating electric field remains active, the frequency of the first alternating electric field decreases while the average amplitude of the first alternating electric field remains constant. The first set of times and the second set of times are mutually exclusive.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
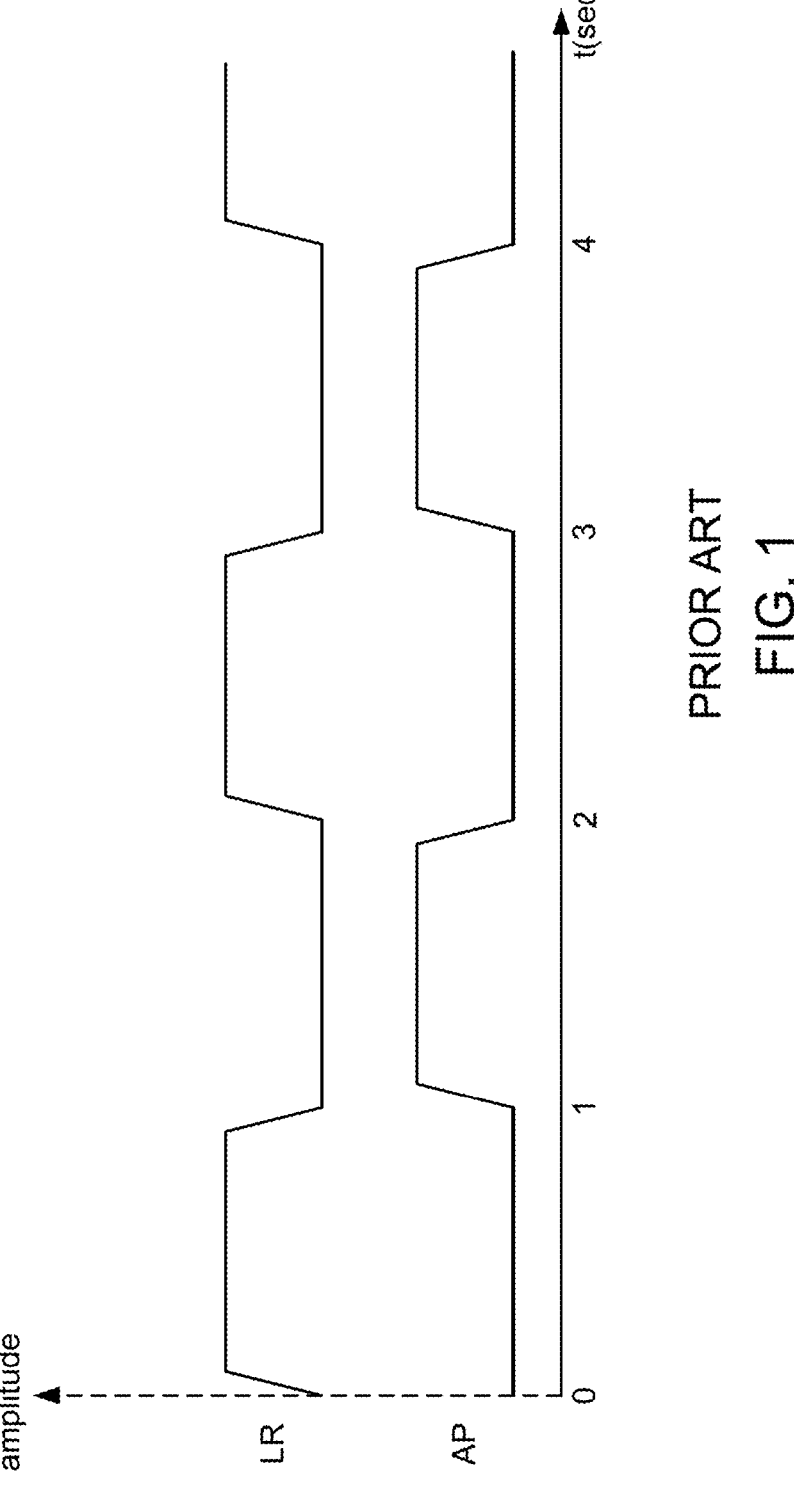
FIG. 1 depicts the AC output amplitudes in two channels of the prior art Optune® system.

FIG. 1 depicts the AC output amplitudes of the L/R channel and the A/P channel in the prior art Optune® system. Notably, when the signal to either the A/P or L/R transducer arrays is turned on during any given one-second interval, the amplitude of the AC voltage does not jump immediately to its peak value. Instead, the amplitude of the AC voltage ramps up from zero to its peak over the course of a 50 ms window. Similarly, when the signal is turned off during any given one-second interval, the amplitude of the AC voltage ramps down from its peak to zero over the course of a 50 ms window.

The inventors have determined that electrosensation is not a problem during steady-state application of an AC voltage to a given pair of transducer arrays, or when the AC voltage turns off/ramps down. Instead, electrosensation appears to only be a problem when the AC voltage turns on/ramps up (which occurs when the system is first turned on and each time the electric field switches direction). The electrosensation is believed to originate from interactions between the alternating electric fields and nerve cells or fibers (i.e., neurons or axons) that are positioned near or adjacent to the transducer arrays.

The inventors have also determined that electrosensation can be ameliorated by using certain patterns of amplitude and frequency changes when the AC voltage is first applied to any given pair of transducer arrays, and also when the alternating electric field switches direction.

More specifically, the inventors have determined that electrosensation can be ameliorated by modifying the ramp-up characteristics so that the amplitude of the AC voltage increases in a series of steps, and allowing some time to pass (e.g., 10-50 ms) for the subject to acclimate to whatever AC voltage is being applied during any given step before the voltage is increased to the next-higher value.

The inventors have also determined that electrosensation can be ameliorated by modifying the ramp-up characteristics by starting out at a frequency that is higher than the recommended frequency for each indication (e.g., higher than 200 kHz for treating glioblastoma), and subsequently decreasing the frequency in a series of steps. The duration of each step should be sufficient (e.g., 10-50 ms) for the subject to acclimate to the frequency that is being applied during any given step before the frequency is decreased to the next-lower value. For example, if the desired final frequency is 200 kHz (e.g., for treating glioblastoma), the frequency could start out at 400 kHz, then drop in successive steps to 350 kHz, 300 kHz, 250 kHz, and then drop once more to the desired target frequency of 200 kHz.

Finally, the inventors have determined that electrosensation can be ameliorated by avoiding (or at least minimizing) situations in which an increase in the amplitude of the AC voltage and a decrease in the frequency of the AC voltage occur simultaneously. This can be implemented by arranging the timing of the amplitude and frequency steps so that that the times when amplitude changes occur and the times when frequency changes occur are always (or at least most of the time) mutually exclusive.

Figure 2:
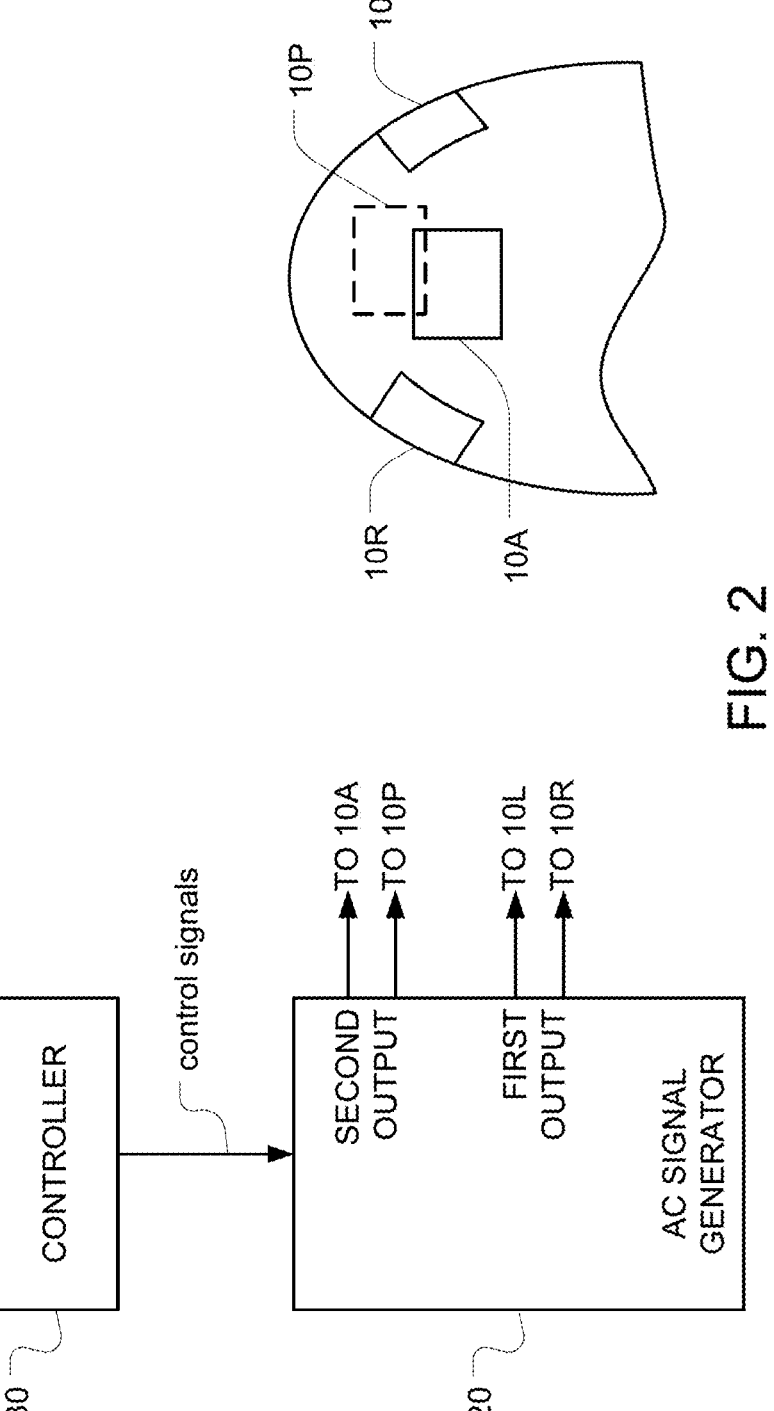
FIG. 2 is a block diagram of a system for driving a set of transducer arrays with AC voltage signals in which the pattern of amplitude and frequency changes of the AC outputs can be controlled.

FIG. 2 is a block diagram of a system for driving a set of transducer arrays with AC voltage signals in which the pattern of amplitude and frequency changes can be controlled. The system includes an AC signal generator 20 that is designed to generate first and second AC outputs at frequencies between 50 kHz and 5 MHz (e.g., 50 kHz-1 MHz, 50-500 kHz, 75-300 kHz, or 150-250 kHz). When the system is used to apply TTFields to a person's body (as shown in FIG. 2), the first AC output is applied across a first pair of transducer arrays 10L and 10R that are positioned to the left and right of the tumor; and the second AC output is applied across a second pair of transducer arrays 10A and 10P that are positioned anterior and posterior to the tumor.

When the AC signal generator 20 applies a voltage between transducer arrays 10L, 10R, an alternating electric field is induced through the target region with field lines that run generally from left to right. And when the AC signal generator 20 applies a voltage between transducer arrays 10A, 10P, an alternating electric field is induced through the target region with field lines that run generally from front to back. The frequency of the alternating electric field will match the frequency of the output of the AC signal generator 20. The electrode elements in the transducer arrays 10 can be, e.g., capacitively-coupled electrode elements (i.e., electrode elements that include a thin dielectric layer that contacts the subject's body) or conductive electrode elements (i.e., electrode elements that include a conductive surface that contacts the subject's body).

In some embodiments, the voltage generated by the AC signal generator 20 is sufficient to induce an electric field of at least 1 V/cm in at least a portion of the cells. In some embodiments, the voltages generated by the AC signal generator 20 is sufficient to induce an electric field of 1-10 V/cm in at least a portion of the cells. In some embodiments, the output current of the AC signal generator 20 is >0.1 A, >0.5 A, >0.7 A, or >1 A (e.g., 0.1-10 A, 0.5-2 A, 0.5-5A, 0.7-2 A, or 0.7-5 A).

As in the prior art Optune® system, (a) the first AC output is applied to the L/R transducer arrays for an interval of time; (b) the second AC output is applied to the A/P transducer arrays for an interval of time; and the two-step sequence (a) and (b) is repeated for the duration of the treatment. But the amplitude and frequency characteristics during the ramp-up periods in the FIG. 2 embodiment differ from the amplitude and frequency characteristics during the ramp-up periods used in Optune® in a manner that helps ameliorate the electrosensation that is experienced by the subject.

The AC signal generator 20 is configured to generate first and second AC outputs with amplitudes and frequencies that depend on a state of at least one control input. The AC signal generator 20 is configured so that the at least one control input controls an amplitude of the first output, a frequency of the first output, an amplitude of the second output, and a frequency of the second output. A controller 30 sends sequential control signals (e.g., at a rate of 1 control signal per ms) to the at least one control input to generate the pattern of amplitude and frequency changes described herein. Note that although FIG. 2 depicts the controller 30 and the AC signal generator 20 as two distinct blocks, those two blocks may be integrated into a single hardware device, as described below.

The details of the construction of the controller 30 and the nature of the control signals will depend on the design of the AC signal generator 20. In one example, the design of the AC signal generator 20 is similar to the AC signal generator described in U.S. Pat. No. 9,910,453 (which is incorporated herein by reference in its entirety), but includes additional hardware that enables it to operate at different frequencies. This particular AC signal generator has two output channels (i.e., a first channel for L/R arrays and a second channel for A/P arrays). The instantaneous AC output voltage on either channel depends on the instantaneous output voltage of a DC-DC converter, and the output voltage of that DC-DC converter is controlled by writing control words to a digital-to-analog converter (DAC), e.g., at a rate of 1 control signal per ms. Frequency selection may be accomplished, for example, by adjusting the timing of various signals within the AC signal generator, and using a bank of switches to swap in appropriate passive components (e.g., inductors and capacitors) that are used to filter out harmonics from the signals. For example, the ability to operate at five different frequencies (e.g., 400 kHz, 350 kHz, 300 kHz, 250 kHz, and 200 kHz) can be implemented by using the bank of switches to swap in a different set of passive components to operate at each of those frequencies.

This AC signal generator can therefore be used to set the AC output voltage and frequency to any desired level (within its operating range) in any desired time pattern by sequentially sending appropriate control words to the DAC, and by sending appropriate control words to the bank of switches to swap in the desired passive components.

Figure 3:
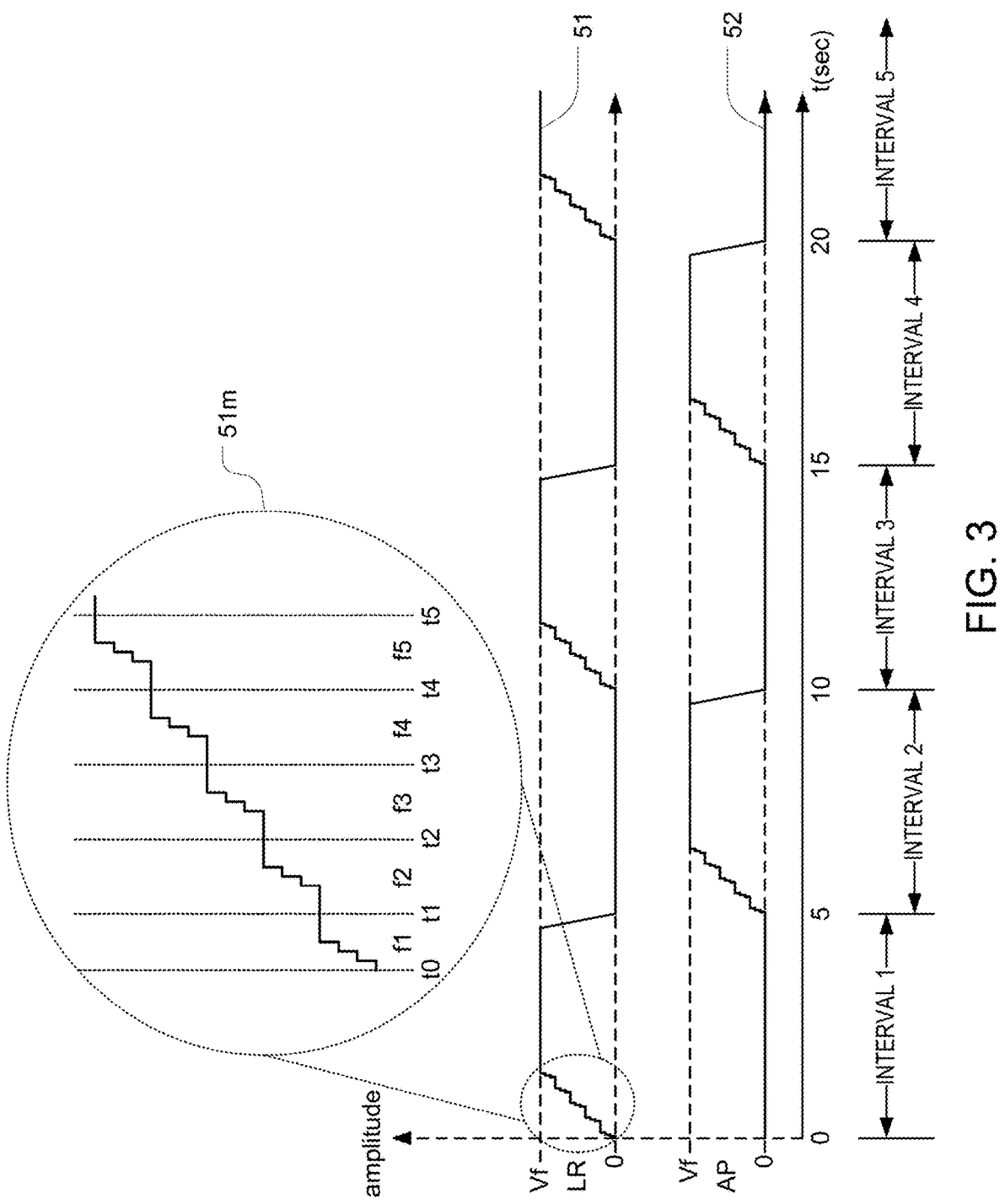
FIG. 3 depicts one example of a pattern of amplitude and frequency changes that can be imparted on the outputs of the AC signal generator over time to ameliorate electrosensation.

FIG. 3 depicts one example of a pattern of amplitude and frequency changes over time that may be imparted on the L/R and A/P output channels of the AC signal generator 20 (shown in FIG. 2) to ameliorate electrosensation. More specifically, trace 51 (together with the accompanying frequency notations f1-f5) depict how the amplitude and frequency of the AC voltage of the L/R or first output channel vary over time, and the situation is similar for trace 52 and the A/P or second output channel. The inset panel 51m is a magnified version of a ramp-up section of trace 51 for the L/R channel during interval 1. The ramp-up sections (not shown) of traces 51 and 52 during the remaining intervals 2, 3, etc. are similar to the depicted ramp-up section for the first interval 1.

In the FIG. 3 example, the L/R channel is active during the odd intervals (i.e., intervals 1, 3, 5 etc.) and the A/P channel is active during the even intervals (i.e., intervals 2, 4, 6, etc.). At the beginning of each interval, there is a ramp-up section between t0 and t5 during which the amplitude of the AC signal generator's respective output (i.e., L/R or A/P) increases in steps from an initial level of 0 V to a final level Vf. And during this ramp-up section, the frequency of the AC signal generator's respective output also decreases from an initial frequency f1 to a final frequency f5. After this ramp-up section, the amplitude remains constant at the final level Vf and the frequency remains constant at the final level f5 until a short time (e.g., 50 ms) before the end of the interval, at which point the amplitude ramps down or drops down to 0 V (while the frequency stays at the final frequency f5 or, alternatively, while the frequency ramps up to the initial frequency f1).

To generate these patterns of amplitude and frequency changes, the controller 30 sequentially sends control words (e.g., once per ms) to the AC signal generator 20. When the AC signal generator 20 receives these control words, it will generate an output with an amplitude and frequency pattern that resembles the waveform depicted in FIG. 3. A similar sequence of control words is used to control the A/P channel.

In the example depicted in FIG. 3, the controller 30 is configured to apply a sequence of control signals to the at least one control input of the AC signal generator 20 during each of the odd intervals of time (e.g., intervals 1, 3, 5, etc.). The sequence of control signals controls the AC signal generator 20 so that when the first output is activated at a given time to, the first output has an initial amplitude and an initial frequency f1. The sequence of control signals also controls the AC signal generator 20 so that at a first set of times that follow the given time while the first output remains active, the amplitude of the first output increases while the frequency of the first output remains constant. In FIG. 3, this first set of times includes the following 15 members: (a) the three increases in amplitude between t0 and t1, (b) the three increases in amplitude between t1 and t2, (c) the three increases in amplitude between t2 and t3, (d) the three increases in amplitude between t3 and t4, and (e) the three increases in amplitude between t4 and t5. Each of these 15 increases in amplitude is clearly visible in the inset 51m of FIG. 3. Each of the increases in amplitude can either be instantaneous or can occur over a period of time (e.g., <50 ms, <20 ms, <10 ms, <5 ms, <2 ms, or <1 ms).

The sequence of control signals also controls the AC signal generator 20 so that at a second set of times that follow the given time while the first output remains active, the frequency of the first output decreases while the amplitude of the first output remains constant. In the inset 51*m* of FIG. 3, this second set of times includes the following four members: t1 (i.e., when the frequency decreases from f1 to f2), t2 (i.e., when the frequency decreases from f2 to f3), t3 (i.e., when the frequency decreases from f3 to f4), and t4 (i.e., when the frequency decreases from f4 to f5). Each of the decreases in frequency can either be instantaneous or can occur over a period of time (e.g., <50 ms, <20 ms, <10 ms, <5 ms, <2 ms, or <1 ms).

Note that in the example depicted in the inset 51*m*, the frequency and amplitude never both change at the same instant, which helps avoid electrosensation. Thus, within interval 1, the first set of times (i.e., the 15 times at which the amplitude changes) and the second set of times (i.e., the four times at which the frequency changes) are mutually exclusive. After t4, the frequency remains at f5 until the end of the interval. The situation is similar for intervals 3, 5, and subsequent odd intervals.

Continuing the example depicted in FIG. 3, the controller 30 is also configured to apply a sequence of control signals to the at least one control input of the AC signal generator 20 during each of the even intervals of time (e.g., intervals 2, 4, etc.). The sequence of control signals further controls the AC signal generator so that (a) when the second output is activated at a certain time, the second output has an initial amplitude and an initial frequency f1, (b) at a third set of times that follow the certain time while the second output remains active, the amplitude of the second output increases while the frequency of the second output remains constant, and (c) at a fourth set of times that follow the certain time while the second output remains active, the frequency of the second output decreases while the amplitude of the second output remains constant. (Note that while FIG. 3 does not include a magnified inset of the ramp-up section of trace 52 for the second output of the AC signal generator 20 (i.e., the A/P channel), the pattern of amplitude and frequency changes for the second output is similar to the pattern described above and depicted in inset 51*m* for the first output of the AC signal generator 20.) And here again, the frequency and amplitude never both change at the same instant, which helps avoid electrosensation. Thus, within interval 2, the third set of times (i.e., the 15 times at which the amplitude changes) and the fourth set of times (i.e., the four times at which the frequency changes) are mutually exclusive. The situation is similar for interval 4 and subsequent even intervals.

The sequence of control signals generated by the controller 30 causes the AC signal generator 20 to (i) activate the first output for an interval of time, (ii) subsequently activate the second output for an interval of time, and (iii) subsequently repeat (i) and (ii) at least 10 times in an alternating sequence (although only the first 2.25 of those repetitions is depicted in FIG. 3).

Although in the example depicted in FIG. 3, the first and third sets of times within a given interval of time each includes 15 times when the amplitude increases and the second and fourth sets of times within a given interval of time each includes 4 times when the frequency decreases (i.e., t1, t2, t3, and t4), the number of members in each of those sets can vary. In some embodiments, each first set of times includes at least 10 times, each second set of times includes at least 3 times, each third set of times includes at least 10 times, and each fourth set of times includes at least 3 times. In other embodiments, each first set of times includes at least 50 times, each second set of times includes at least 3 times, each third set of times includes at least 50 times, and each fourth set of times includes at least 3 times.

In the example depicted in FIG. 3, each interval of time when the first output is activated (intervals 1, 3, 5, etc.) is 5 s long, and each interval of time when the second output is activated (intervals 2, 4, etc.) is 5 s long. But in alternative embodiments, the duration of those intervals can be different (e.g., between 5 and 60 s, between 1 and 5 s, or at least 2 s). For example, each interval of time when the first output is activated can have a duration of at least 800 ms, and each interval of time when the second output is activated can have a duration of at least 800 ms.

In the example depicted in FIG. 3, each first set of times and a respective second set of times are interspersed with each other using the following pattern: aaafaaafaaafaaafaaa (where "a" denotes an amplitude change and "f" denotes a frequency change). And each third set of times and a respective fourth set of times are interspersed with each other using the same pattern. But in alternative embodiments, those sets of times need not be interspersed. For example, the amplitude could change 15 times until the amplitude reaches Vf while the frequency remains constant at f1, and subsequently the frequency could change four times until the frequency reaches f5 (in which case the pattern would be aaaaaaaaaaaaaaaffff. A wide variety of alternative patterns may also be used, including but not limited to ffffaaaaaaaaaaaaaaa, afafafafafa, affaffaffaffa, etc.

In some embodiments, the initial frequency f1 of the first output is at least 50% higher than the final frequency f5 of the first output, and the initial frequency of the second output is at least 50% higher than the final frequency of the second output. For example, in the context of treating glioblastoma, the initial frequency f1 could be 400 kHz, and the final frequency f5 could be 200 kHz. But in alternative embodiments, the initial frequency of both the first and second outputs could be only at least 25% higher than the final frequency for those outputs.

In some embodiments, the final frequency of the first and second outputs is between 75 kHz and 300 kHz. These embodiments include, for example, using a final frequency of 200 kHz to treat glioblastoma or ovarian cancer, using a final frequency of 150 kHz to treat mesothelioma, non-small cell lung cancer, or liver cancer, and using a final frequency between 75 kHz and 190 kHz (or between 75 kHz and 220 kHz) to increase the permeability of the subject's blood brain barrier.

A wide variety of alternative designs for the AC signal generator 20 and the controller 30 can be substituted for the examples provided above, as long as the controller 30 has the ability to control the AC signal generator 20. For example, if the AC signal generator is designed to respond to an analog control signal, the controller 30 must generate whatever sequence of analog control signals is needed to cause the AC signal generator 20 to output the desired waveforms. In this situation, the controller 30 could be implemented using a microprocessor or microcontroller that is programmed to write appropriate control words to a digital-to-analog converter, the output of which generates the analog control signals that cause the AC signal generator 20 to generate the desired waveforms. Alternatively, the controller 30 could be implemented using an analog circuit that automatically generates the appropriate sequence of control signals (which are then applied to the control input of the AC signal generator).

The pattern of amplitude increases and frequency decreases in AC voltage depicted in the inset panel 51*m* of FIG. 3 is not the only pattern that can be used to ameliorate electrosensation. To the contrary, a variety of alternative patterns can be used. For example, while trace 51 shows that each of the amplitude changes has the same magnitude, the magnitude of the amplitude changes within the first set of times (or the third set of times) can vary. Similarly, the timing between successive amplitude steps within the first set of times (or the third set of times) can be consistent or inconsistent. The magnitude of each frequency step within the second set of times (or the fourth set of times) can be consistent or inconsistent, and the timing between successive frequency steps within the second set of times (or the fourth set of times) can be consistent or inconsistent.

Figure 4:
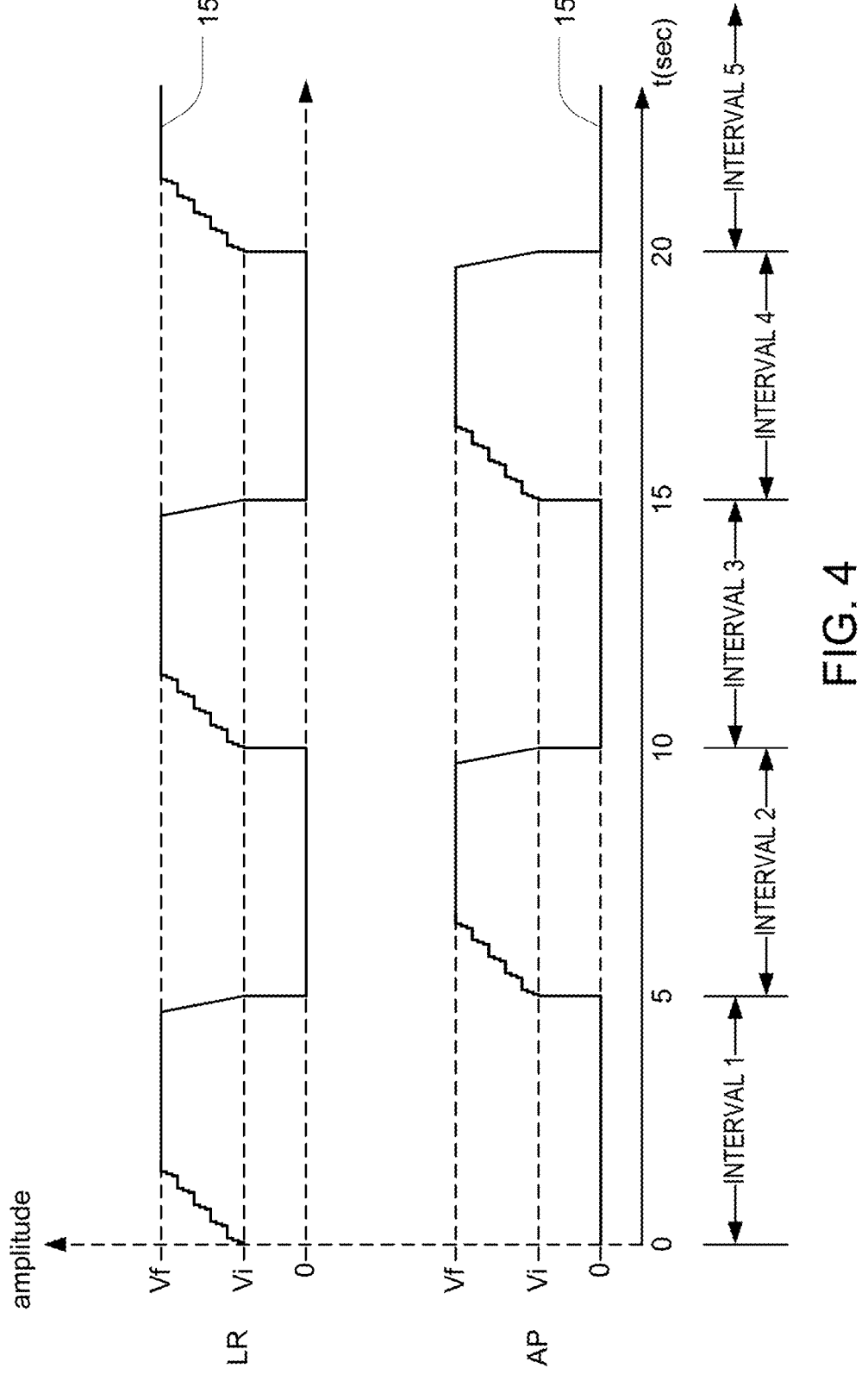
FIG. 4 depicts another example of a pattern of amplitude and frequency changes that can be imparted on the outputs of the AC signal generator over time to ameliorate electrosensation.

In the example described above in connection with FIG. 3, the amplitude of the AC signal generator's first and second outputs are both very small (e.g., less than 1% of Vf) when the first and second intervals of time begin. Similarly, the corresponding first and second alternating electric fields are both very small (e.g., less than 1% of the final field strength) when the first and second intervals of time begin. But in alternative embodiments (e.g., as depicted in FIG. 4), the amplitude of the AC signal generator's first and second outputs can jump immediately to an initial level Vi that is 20-80% of the final level Vf.

These embodiments are advantageous because electrosensation is relatively rare when the voltage is below a threshold level (e.g., 40 V). Accordingly, jumping immediately from 0 V to an initial voltage Vi (e.g., 40 V) when the first and second intervals of time begin (as depicted in FIG. 4) will not cause electrosensation in the vast majority of patients. Because time is not wasted ramping up from 0 V to Vi, more time will be available to ramp up from Vi to the final voltage Vf (which can be e.g., over 100 V). This will advantageously (a) increase the average field strength that is applied to the subject, (b) provide the subject with more time to get used to each new voltage level before the voltage increases to the next level, and (c) provide the subject with more time to get used to each new frequency level before the frequency decreases to the next level, thereby further ameliorating electrosensation.

In some embodiments, the value of the initial level Vi will be the same for all patients (e.g., 40 V). In other embodiments, the value of the initial level Vi can be patient-specific and can be set via a suitable user interface that communicates with the controller 30. In the latter embodiments, the controller 30 can be programmed to apply different voltage levels to the subject in order to determine the threshold voltage Vth where electrosensation begins for the particular subject that will be treated. The initial level Vi is then set below that threshold Vth during the course of treatment for that particular subject.

In the examples described above, the direction of the alternating electric fields was switched between two directions. But in alternative embodiments the direction of the alternating electric fields may be switched between three or more directions (assuming that additional pairs of transducer arrays are provided). For example, the direction of the alternating electric fields may be switched between three directions, each of which is determined by the placement of its own pair of transducer arrays. In other alternative embodiments, the transducer arrays need not be arranged in pairs. See, for example, the transducer array positioning described in U.S. Pat. No. 7,565,205, which is incorporated herein by reference. But regardless of the arrangement of the transducer arrays, one of the patterns of amplitude and frequency changes described herein is used every time a given transducer array is activated.

In some anatomic locations, the transducer arrays are not positioned on the subject's skin. Instead, the transducer arrays are implanted into the subject's body (e.g., just beneath the subject's skin) so that application of an AC voltage between the transducer arrays will impose the alternating electric fields in a target region of the subject's body.

In some anatomic locations, instead of switching the orientation of the alternating electric field back and forth between two or more different directions, an electric field with a constant orientation may be used. Embodiments for use with these locations are similar to the FIG. 2 embodiment, except that the AC signal generator 20 has only a single output (e.g., only the L/R output). In these embodiments, the AC voltage generator is configured to, when initially switched on, increase its output voltage using any of the patterns described above (e.g., in connection with the inset panel 51*m* in FIG. 3), and then either leave its output voltage and frequency at fixed levels for the duration of the treatment, or switch the single output on and off repeatedly (e.g., on for 1-60 s and off for 0.1-10 s), or occasionally (e.g., on for 6 or more hours and off for 1-4 hours, for example for shower breaks or to replace the arrays). In the latter situation, each time the AC voltage generator switches back on, it increases its output voltage and decreases its frequency from an initial level to a final level using any of the patterns described above (e.g., in connection with the inset panel 51*m* in FIG. 3).

Finally, the apparatuses described above (e.g., in connection with FIGS. 2-3 or FIGS. 2 and 4) can be used to perform the following steps (i) through (iii): (i) imposing a first alternating electric field with a first orientation in the target region for an interval of time, wherein the first alternating electric field has a frequency and an average amplitude that vary over time such that (a) when the first alternating electric field is activated at a given time, the first alternating electric field has an initial average amplitude and an initial frequency, (b) at a first set of times that follow the given time while the first alternating electric field remains active, the average amplitude of the first alternating electric field increases while the frequency of the first alternating electric field remains constant, and (c) at a second set of times that follow the given time while the first alternating electric field remains active, the frequency of the first alternating electric field decreases while the average amplitude of the first alternating electric field remains constant, wherein the first set of times and the second set of times are mutually exclusive; (ii) subsequently imposing a second alternating electric field with a second orientation in the target region for an interval of time, wherein the second alternating electric field has a frequency and an average amplitude that vary over time such that (a) when the second alternating electric field is activated at a certain time, the second alternating electric field has an initial average amplitude and an initial frequency, (b) at a third set of times that follow the certain time while the second alternating electric field remains active, the average amplitude of the second alternating electric field increases while the frequency of the second alternating electric field remains constant, and (c) at a fourth set of times that follow the certain time while the second alternating electric field remains active, the frequency of the second alternating electric field decreases while the average amplitude of the second alternating electric field remains constant, wherein the third set of times and the fourth set of times are mutually exclusive; and (iii) subsequently repeating steps (i) and (ii) at least 10 times in an alternating sequence.

The embodiments and methods described herein can advantageously be used to ameliorate electrosensation when a subject is being treated using alternating electric fields. And ameliorating electrosensation can be extremely beneficial because it enables the subject to tolerate higher amplitudes and/or lower frequencies (as compared to the amplitudes and frequencies that the subject could tolerate without relying on the embodiments and methods described herein).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying electrical signals to first, second, third and fourth sets of at least one electrode element, the apparatus comprising:

an AC signal generator having a first output for applying an AC voltage between the first set of at least one electrode element and the second set of at least one electrode element, a second output for applying an AC voltage between the third set of at least one electrode element and the fourth set of at least one electrode element, and at least one control input, wherein the AC signal generator is configured so that the at least one control input controls an amplitude of the first output, a frequency of the first output, an amplitude of the second output, and a frequency of the second output; and a controller configured to apply a sequence of control signals to the at least one control input of the AC signal generator, wherein the sequence of control signals controls the AC signal generator so that (a) when the first output is activated at a given time, the first output has an initial amplitude and an initial frequency, (b) at a first set of times that follow the given time while the first output remains active, the amplitude of the first output increases while the frequency of the first output remains constant, and (c) at a second set of times that follow the given time while the first output remains active, the frequency of the first output decreases while the amplitude of the first output remains constant, wherein the first set of times and the second set of times are mutually exclusive, wherein the sequence of control signals further controls the AC signal generator so that (a) when the second output is activated at a certain time, the second output has an initial amplitude and an initial frequency, (b) at a third set of times that follow the certain time while the second output remains active, the amplitude of the second output increases while the frequency of the second output remains constant, and (c) at a fourth set of times that follow the certain time while the second output remains active, the frequency of the second output decreases while the amplitude of the second output remains constant, wherein the third set of times and the fourth set of times are mutually exclusive, and wherein the sequence of control signals causes the AC signal generator to (i) activate the first output for an interval of time, (ii) subsequently activate the second output for an interval of time, and (iii) subsequently repeat (i) and (ii) at least 10 times in an alternating sequence, whereby there will be at least 10 activations of the first output and at least 10 activations of the second output, wherein each of the at least 10 activations of the first output corresponds to a respective first set of times and a respective second set of times, and wherein each of the at least 10 activations of the second output corresponds to a respective third set of times and a respective fourth set of times.

2. The apparatus of claim 1, wherein each of the respective first sets of times includes at least 10 times, each of the respective second sets of times includes at least 3 times, each of the respective third sets of times includes at least 10 times, and each of the respective fourth sets of times includes at least 3 times.

3. The apparatus of claim 1, wherein each of the respective first sets of times includes at least 50 times, each of the respective second sets of times includes at least 3 times, each of the respective third sets of times includes at least 50 times, and each of the respective fourth sets of times includes at least 3 times.

4. The apparatus of claim 1, wherein each interval of time when the first output is activated has a duration of at least 800 ms, and wherein each interval of time when the second output is activated has a duration of at least 800 ms.

5. The apparatus of claim 1, wherein the first sets of times and the second sets of times are interspersed with each other, and wherein the third sets of times and the fourth sets of times are interspersed with each other.

6. The apparatus of claim 1, wherein the initial frequency of the first output is at least 50% higher than a final frequency of the first output, and wherein the initial frequency of the second output is at least 50% higher than a final frequency of the second output.

7. The apparatus of claim 6, wherein the final frequency of the first output is between 75 kHz and 300 kHz, and wherein the final frequency of the second output is between 75 kHz and 300 kHz.

8. The apparatus of claim 1, wherein each of the respective first sets of times includes at least 50 times, each of the respective second sets of times includes at least 3 times, each of the respective third sets of times includes at least 50 times, and each of the respective fourth sets of times includes at least 3 times, wherein each interval of time when the first output is activated has a duration of at least 2 seconds, wherein each interval of time when the second output is activated has a duration of at least 2 seconds, wherein the first sets of times and the second sets of times are interspersed with each other, wherein the third sets of times and the fourth sets of times are interspersed with each other, wherein the initial frequency of the first output is at least 50% higher than a final frequency of the first output, and wherein the initial frequency of the second output is at least 50% higher than a final frequency of the second output.

9. The apparatus of claim 8, wherein the final frequency of the first output is between 75 kHz and 300 kHz, and wherein the final frequency of the second output is between 75 kHz and 300 kHz.

10. An apparatus for applying electrical signals to first and second sets of at least one electrode element, the apparatus comprising:

an AC signal generator having (i) an output for applying an AC voltage between the first set of at least one electrode element and the second set of at least one electrode element and (ii) at least one control input, wherein the AC signal generator is configured so that the at least one control input controls an amplitude of the output and a frequency of the output; and a controller configured to apply a sequence of control signals to the at least one control input of the AC signal generator, wherein the sequence of control signals controls the AC signal generator so that (a) when the output is activated at a given time, the output has an initial amplitude and an initial frequency, (b) at a first set of times that follow the given time while the output remains active, the amplitude of the output increases while the frequency of the output remains constant, and (c) at a second set of times that follow the given time while the output remains active, the frequency of the output decreases while the amplitude of the output remains constant, wherein the first set of times and the second set of times are mutually exclusive, wherein the first set of times includes at least 10 times, wherein the second set of times includes at least 3 times, wherein the first set of times and the second set of times are interspersed with each other, wherein the initial frequency of the output is at least 50% higher than a final frequency of the output, and wherein the final frequency of the output is between 75 kHz and 300 kHz.

* * * * *